(12) United States Patent
Leenslag et al.

(10) Patent No.: US 6,433,034 B1
(45) Date of Patent: Aug. 13, 2002

(54) FLEXIBLE POLYURETHANE FOAMS

(75) Inventors: Jan Willem Leenslag, Tremelo; Anthony Cunningham, Leefdaal; Berend Eling, Bertem, all of (BE)

(73) Assignee: Imperial Chemical Industries PLC, London (GB)

( * ) Notice: Subject to any disclaimer, the term of this patent is extended or adjusted under 35 U.S.C. 154(b) by 0 days.

(21) Appl. No.: 09/989,451

(22) Filed: Nov. 21, 2001

Related U.S. Application Data

(60) Division of application No. 09/197,978, filed on Nov. 23, 1998, now Pat. No. 6,335,379, which is a division of application No. 08/641,122, filed on Apr. 30, 1996, now Pat. No. 5,900,442, which is a continuation-in-part of application No. 08/481,725, filed on Jun. 7, 1995, now abandoned.

(30) Foreign Application Priority Data

May 12, 1995 (EP) .............................. 95201246

(51) Int. Cl.⁷ .................................. C08J 9/36
(52) U.S. Cl. ........................ 521/174; 521/170
(58) Field of Search ................... 521/170, 174

(56) References Cited

U.S. PATENT DOCUMENTS

| | | | |
|---|---|---|---|
| 3,159,700 A | 12/1964 | Nakamura | 264/321 |
| 4,454,248 A | 6/1984 | Pollock et al. | 521/53 |
| 4,478,960 A | 10/1984 | Buethe et al. | 521/126 |
| 4,833,176 A | 5/1989 | Wolf et al. | 521/160 |
| 5,084,486 A | 1/1992 | Patten et al. | |
| 5,260,347 A | 11/1993 | Krueger et al. | 521/164 |
| 5,538,779 A | 7/1996 | Mispreuve et al. | 428/220 |
| 5,900,442 A | 5/1999 | Leenslag et al. | 521/174 |
| 6,020,390 A | 2/2000 | Leenslag | 521/155 |

FOREIGN PATENT DOCUMENTS

| | | |
|---|---|---|
| CA | 2091952 | 9/1993 |
| EP | 0010850 | 5/1980 |
| EP | 2040948 | 9/1980 |
| EP | 0022617 | 1/1981 |
| EP | 0309217 | 3/1989 |
| EP | 0309218 | 3/1989 |
| EP | 0392788 | 10/1990 |
| EP | 0442631 | 8/1991 |
| EP | 0567027 | 4/1993 |
| EP | 0641635 | 3/1995 |
| GB | 2096616 | 10/1982 |
| WO | 9212197 | 7/1992 |
| WO | 9407942 | 4/1994 |

*Primary Examiner*—John M. Cooney, Jr.
(74) *Attorney, Agent, or Firm*—Pillsbury Winthrop LLP

(57) ABSTRACT

Process for preparing a flexible polyurethane foam by reacting a polyisocyanate and two different polyols under foam forming conditions so as to prepare a rigid foam and by crushing the rigid foam so obtained. Flexible foams are obtained which do not show a major glass transition temperature between −100° C. and +25° C.

4 Claims, No Drawings

FLEXIBLE POLYURETHANE FOAMS

This application is a Divisional of U.S. application Ser. No. 09/197,978 filed Nov. 23, 1998 which is now U.S. Pat. No. 6,335,379, which is a Divisional of U.S. application Ser. No. 08/641,122 filed Apr. 30, 1996 which is now U.S. Pat. No. 5,900,442, which is a continuation-in-part of U.S. application Ser. No. 08/481,725 filed Jun. 7, 1995 abandoned.

The present invention is concerned with flexible polyurethane foams and a process to prepare such flexible polyurethane foams.

Flexible polyurethane foams are widely known. Such foams show a relatively high resilience (ball rebound), a relatively low modulus, a relatively high sag factor and a relatively low hysteresis loss.

Such foams further show a major glass-rubber transition below ambient temperature, generally in the temperature range of −100° C. to −10° C. The commonly applied relatively high molecular weight polyether and polyester polyols in such foams are responsible for the sub-ambient glass transition temperature ($Tg^s$). These polyether and polyester polyols are often referred to as soft segments. Above $Tg^s$ the foam displays its typical flexible properties until softening and/or melting of the isocyanate-derived urethane/urea clusters ("hard domains") takes place. This softening and/or melting temperature ($Tg^h$ and/or $Tm^h$) often coincides with the onset of thermal degradation of polymer segments. The $Tg^h$ and/or $Tm^h$ for flexible polyurethane foams is generally higher than 100° C., often even exceeding 200° C. At the $Tg^s$ a sharp decrease of the modulus of the flexible foam is observed. Between $Tg^s$ and $Tg^h/Tm^h$ the modulus remains fairly constant with increasing temperature and at $Tg^h/Tm^h$ again a substantial decrease of the modulus takes place. A way of expressing the presence of $Tg^s$ is to determine the ratio of the Young's storage modulus E' at −100° C. and +25° C. as per Dynamic Mechanical Thermal Analysis (DMTA measured according to ISO/DIS 6721-5). For conventional flexible polyurethane foams the $$\frac{E' - 100° \text{ C.}}{E' + 25° \text{ C.}} \text{ ratio is at least 25.}$$

Another feature of $Tg^s$ by DMTA (ISO/DIS 6721-5) is that for conventional flexible polyurethane foams the maximum value of the $$\text{ratio of } \frac{\text{Young's loss modulus } E''}{\text{Young's storage modulus } E'} (\tan\delta_{max}) \text{ over the}$$

−100° C./+25° C. temperature range varies from 0.20–0.80 in general. The Young's loss modulus E" is measured by DMTA (ISO/DIS 6721-5) as well.

In the context of the present application a polyurethane foam is regarded as flexible when the ball rebound (measured according to ISO 8307 with the proviso that no preflex conditioning is applied, that only one rebound value per sample is measured and that test pieces are conditioned at 23° C.±2° C., (50±5% relative humidity) is at least 40%, preferably at least 50% and most preferably 55–85% in at least one of the three dimensional directions. If in the present application ISO 8307 is mentioned it refers to the test as described above including the provisos. Preferably such flexible foams have a Young's storage modulus at 25° C. of at most 500 kPa, more preferably at most 350 kPa and most preferably between 10 and 200 kPa (Young's storage modulus measured by DMTA according to ISO/DIS 6721-5). Further, such flexible foams preferably have a sag factor (CLD 65/25) of at least 2.0, more preferably at least 3.5 and most preferably 4.5–10 (measured according to ISO 3386/1). Still further such flexible foams preferably have a CLD hysteresis loss (ISO 3386/1) of below 55%, more preferably below 50% and most preferably below 45%.

In the context of the present patent application polyurethane foams are considered as rigid if the ball rebound is below 40%, as measured according to ISO 8307, at a free rise core density of the foam of 3–27 kg/m³.

Preferably the ratio $E'_{-100° C.}/E'_{+25° C.}$ of such a rigid foam is 1.3–15. Conventional flexible foams are made by reacting a polyisocyanate and a relatively high molecular weight isocyariate reactive polymer, often a polyester or polyether polyol, in the presence of a blowing agent and optionally further using limited amounts of relatively low molecular weight chain extenders and cross-linkers and optionally using additives like catalysts, surfactants, fire retardants, stabilisers and antioxidants. The relatively high molecular weight isocyanate reactive polymer in general represents the highest weight fraction of the foam. Such flexible foams may be prepared according to the one-shot, the quasi- or semi-prepolymer or the prepolymer process. Such flexible foams may be moulded foams or slabstock foams and may be used as cushioning material in furniture and automotive seating and in mattresses, as carpet backing, as hydrophilic foam in diapers and as packaging foam. Further they may be used for acoustic applications, e.g. sound insulation. Examples of prior art for these conventional flexible foams are EP-10850, EP-22617, BP-111121, EP-296449, EP-309217, EP-309218, EP-392788 and EP-442631.

Conventional rigid foams are made in a similar way with the proviso that often the polyisocyanates have a higher isocyanate functionality, the amount of high molecular weight polyols used is lower and the amount and functionality of the cross-linkers is higher.

WO92/12197 discloses an energy-absorbing, open-celled, water-blown, rigid polyurethane foam obtained by reacting a polyurethane foam formulation, comprising water which acts as a blowing agent and a cell-opener, in a mould wherein the cured foam has a moulded density of about 32 to 72 kg/m³ and a crush strength which remains constant from 10 to 70% deflection at loads of less than 70 psi. The foams have minimal spring back or hysteresis.

GB2096616 discloses a directionally flexibilized, rigid, closed-cell plastic foam. The rigid foams are flexibilized in order to use them for e.g. pipe-insulation. Cells should remain closed.

U.S. Pat. No. 4,299,883 discloses a sound-absorbent material made by compressing a foam having closed cells to such an extent that the foam recovers to 50–66% of its original thickness. By the compression the cells are ruptured and the foam becomes flexible and resilient; it may replace felt. The disclosure mainly refers to polycarbodiimide foams.

EP561216 discloses the preparation of foam boards having improved heat insulation properties, wherein the foam has anisotropic cells having a length ratio of the long and the small axis of 1.2–1.6 and a density of 15–45 kg/m³ and wherein the cells have been crushed in the direction of the plate thickness. The disclosure actually refers to polystyrene boards. Since the disclosure refers to foams having improved heat-insulation properties, the foams actually have closed cells.

EP641635 discloses a process for preparing foam boards, having a dynamic stiffness of at most 10 MN/m³, by crushing a board of 17–30 kg/m³ density at least twice to 60–90% of its original thickness. Preferably closed-celled polystyrene is used. In the examples it is shown that a polystyrene foam which has been crushed showed a better heat insulation than an uncrushed one.

U.S. Pat. No. 4,454,248 discloses a process for preparing a rigid polyurethane foam wherein a partially cured rigid foam is softened, then crushed and re-expanded and fully cured.

Surprisingly a completely new class of flexible polyurethane foams was found such foams having no major glass-rubber transition between −100° C. and +25° C. In more quantitative terms these foams show a ratio $E'_{-100°\,C.}/E'_{+25°\,C.}$ of 1.3 to 15.0, preferably of 1.5 to 10 and most preferably of 1.5 to 7.5. The $\tan \delta_{max}$ over the −100° C. to +25° C. temperature range is below 0.2.

The free rise core density of such foams may range from 4–30 kg/m³ and preferably ranges from 4–20 kg/m³ (measured according to ISO/DIS845). Preferably the foams according to the present invention have a major glass transition above 50° C. and most preferably above 80° C.

The flexible polyurethane foams according to the present invention are prepared by reacting a polyisocyanate and a polyfunctional isocyanate-reactive polymer under foam forming conditions to prepare a rigid polyurethane foam and by crushing this rigid polyurethane foam. Further the present invention is concerned with the process for preparing such rigid foams and with reaction systems comprising the ingredients for making such foams.

In the context of the present invention the following terms have the following meaning:

1) isocyanate index or NCO index or index:
   the ratio of NCO-groups over isocyanate-reactive hydrogen atoms present in a formulation, given as a percentage:

$$\frac{[NCO] \times 100}{[active\ hydrogen]}(\%).$$

In other words the NCO-index expresses the percentage of isocyanate actually used in a formulation with respect to the amount of isocyanate theoretically required for reacting with the amount of isocyanate-reactive hydrogen used in a formulation.

It should be observed that the isocyanate index as used herein is considered from the point of view of the actual foaming process involving the isocyanate ingredient and the isocyanate-reactive ingredients. Any isocyanate groups consumed in a preliminary step to produce modified polyisocyanates (including such isocyanate-derivatives referred to in the art as quasi or semi-prepolymers and prepolymers) or any active hydrogens consumed in a preliminary step (e.g. reacted with isocyanate to produce modified polyols or polyamines) are not taken into account in the calculation of the isocyanate index. Only the free isocyanate groups and the free isocyanate-reactive hydrogens (including those of the water) present at the actual foaming stage are taken into account.

2) The expression "isocyanate-reactive hydrogen atoms" as used herein for the purpose of calculating the isocyanate index refers to the total of active hydrogen atoms in hydroxyl and amine groups present in the reactive compositions; this means that for the purpose of calculating the isocyanate index at the actual foaming process one hydroxyl group is considered to comprise one reactive hydrogen, one primary amine group is considered to comprise one reactive hydrogen and one water molecule is considered to comprise two active hydrogens.

3) Reaction system: a combination of components wherein the polyisocyanates are kept in one or more containers separate from the isocyanate-reactive components.

4) The expression "polyurethane foam" as used herein refers to cellular products as obtained by reacting polyisocyanates with isocyanate-reactive hydrogen containing compounds, using foaming agents, and in particular includes cellular products obtained with water as reactive foaming agent (involving a reaction of water with isocyanate groups yielding urea linkages and carbon dioxide and producing polyurea-urethane foams) and with polyols, aminoalcohols and/or polyamines as isocyanate-reactive compounds.

5) The term "average nominal hydroxyl functionality" is used herein to indicate the number average functionality (number of hydroxyl groups per molecule) of the polyol or polyol composition on the assumption that this is the number average functionality (number of active hydrogen atoms per molecule) of the initiators used in their preparation although in practice it will often be somewhat less because of some terminal unsaturation.

6) The word "average" refers to number average unless indicated otherwise.

The foams according to the present invention are prepared by reacting a polyisocyanate (1), an isocyanate-reactive compound (2), said compound (2) having an average equivalent weight of at most 374 and an average number of isocyanate-reactive hydrogen atoms of from 2 to 8, an isocyanate-reactive compound (3), said compound (3) iS having an average equivalent weight of more than 374 and an average number of isocyanate-reactive hydrogen atoms of from 2 to 6 and water to prepare a rigid polyurethane foam and by crushing this rigid polyurethane foam.

Further the present invention is concerned with reaction systems comprising the above ingredients. The present invention is also concerned with a process for preparing rigid polyurethane foams using the above ingredients. More in particular the foams according to the present invention are prepared by reacting a polyisocyanate (1), a polyol (2) having a hydroxyl number of at least 150 mg KOH/g and an average nominal hydroxyl functionality of from 2 to 8, a polyol (3) having a hydroxyl number of from 10 to less than 150 mg KOH/g and an average nominal hydroxyl functionality of from 2 to 6 and water to prepare a rigid polyurethane foam and by crushing this rigid polyurethane foam.

Suitable organic polyisocyanates for use in the process of the present invention include any of those known in the art for the preparation of rigid polyurethane foams, like aliphatic, cycloaliphatic, araliphatic and, preferably, aromatic polyisocyanates, such as toluene diisocyanate in the form of its 2,4 and 2,6-isomers and mixtures thereof and diphenylmethane diisocyanate in the form of its 2,4'-, 2,2'- and 4,4'-isomers and mixtures thereof, the mixtures of diphenylmethane diisocyanates (MDI) and oligomers thereof having an isocyanate functionality greater than 2 known in the art as "crude" or polymeric MDI (polymethylene polyphenylene polyisocyanates), the known variants of MDI comprising urethane, allophanate, urea, biuret, carbodiimide, uretonimine and/or isocyanurate groups.

Isocyanate-reactive compounds (2) include any of those known in the art for that purpose like polyamines, aminoalcohols and polyols. of particular importance for the preparation of the rigid foams are polyols and polyol mixtures having hydroxyl numbers of at least 150 mg KOH/g and an average nominal hydroxyl functionality of from 2 to 6.

Suitable polyols have been fully described in the prior art and include reaction products of alkylene oxides, for example ethylene oxide and/or propylene oxide, with initiators containing from 2 to 8 active hydrogen atoms per molecule. Suitable initiators include: polyols, for example ethylene glycol, diethylene glycol, propylene glycol, dipropylene glycol, butane diol, glycerol, trimethylolpropane, triethanolamine, pentaerythritol, sorbitol and sucrose; polyamines, for example ethylene diamine, tolylene diamine, diaminodiphenylmethane and polymethylene polyphenylene polyamines; and aminoalcohols, for example ethanolamine and diethanolamine; and mixtures of such initiators. Other suitable polyols include polyesters obtained by the condensation of appropriate proportions of glycols and higher functionality polyols with polycarboxylic acids. Still further suitable polyols include hydroxyl terminated polythioethers, polyamides, polyesteramides, polycarbonates, polyacetals, polyolefins and polysiloxanes. Still further suitable isocyanate-reactive compounds include ethylene glycol, diethylene glycol, propylene glycol, dipropylene glycol, butane diol, glycerol, trimethylolpropane, ethylene diamine, ethanolamine, diethanolamine, triethanolamine and the other initiators mentioned before. Mixtures of such isocyanate-reactive compounds may be used as well.

Isocyanate-reactive compounds (3) include any of those known in the art for that purpose, like polyamines, aminoalcohols and polyols. of particular importance for the preparation of the rigid foams are polyols and polyol mixtures having a hydroxyl value of 10 to less than 150 and preferably of 15–60 mg KOH/g and an average nominal hydroxyl functionality of from 2 to 6 and preferably of from 2 to 4. These high molecular weight polyols are generally known in the art and include reaction products of alkylene oxides, for example ethylene oxide and/or propylene oxide, with initiators containing from 2 to 6 active hydrogen atoms per molecule. Suitable initiators include: polyols, for example ethylene glycol, diethylene glycol, propylene glycol, dipropylene glycol, butane diol, glycerol, trimethylolpropane, triethanolamine, pentaerythritol and sorbitol; polyamines, for example ethylene diamine, tolylene diamine, diaminodiphenylmethane and polymethylene polyphenylene polyamines; and aminoalcohols, for example ethanolamine and diethanolamine; and mixtures of such initiators. Other suitable polyols include polyesters obtained by the condensation of appropriate proportions of glycols and higher functionality polyols with polycarboxylic acids. Still further suitable polyols include hydroxyl terminated polythioethers, polyamides, polyesteramides, polycarbonates, polyacetals, polyolefins and polysiloxanes. Preferred polyols are the polyether polyols comprising ethylene oxide and/or propylene oxide units and most preferably polyoxyethylene polyoxypropylene polyols having an oxyethylene content of at least 20% by weight. Other polyols which may be used comprise dispersions or solutions of addition or condensation polymers in polyols of the types described above. Such modified polyols, often referred to as "polymer" polyols have been fully described in the prior art and include products obtained by the in situ polymerisation of one or more vinyl monomers, for example styrene and acrylonitrile, in polymeric polyols, for example polyether polyols, or by the in situ reaction between a polyisocyanate and an amino- or hydroxy-functional compound, such as triethanolamine, in a polymeric polyol.

The polymer modified polyols which are particularly interesting in accordance with the invention are products obtained by in situ polymerisation of styrene and/or acrylonitrile in poly(oxyethylene/oxypropylene) polyols and products obtained by in situ reaction between a polyisocyanate and an amino or hydroxy-functional compound (such as triethanolamine) in a poly(oxyethylene/oxypropylene) polyol. Polyoxyalkylene polyols containing from 5 to 50% of dispersed polymer are particularly useful. Particle sizes of the dispersed polymer of less than 50 microns are preferred. Mixtures of such isocyanate-reactive compounds may be used as well.

The relative amount of isocyanate-reactive compound (2) and (3) or polyol (2) and (3) may vary widely and preferably ranges from 0.1:1 to 4:1 (w:w).

The relative quantities of the polyisocyanate and the isocyanate-reactive compounds to be reacted may vary within a wide range. In general an isocyanate index will be applied of from 25 to 300, preferably of from 30 to 200 and most preferably of from 40 to 150.

In order to prepare a foam water is used as a blowing agent. However if the amount of water is not sufficient to obtain the desired density of the foam any other known way to prepare polyurethane foams may be employed additionally, like the use of reduced or variable pressure, the use of a gas like air, $N_2$ and $CO_2$, the use of more conventional blowing agents like chlorofluorocarbons, hydrofluorocarbons, hydrocarbons and fluorocarbons, the use of other reactive blowing agents, i.e. agents which react with any of the ingredients in the reacting mixture and due to this reaction liberate a gas which causes the mixture to foam and the use of catalysts which enhance a reaction which leads to gas formation like the use of carbodiimide-formation-enhancing catalysts such as phospholene oxides. Combinations of these ways to make foams may be used as well. The amount of blowing agent may vary widely and primarily depends on the desired density. Water may be used as liquid at below-ambient, ambient or elevated temperature and as steam.

Per 100 parts by weight of polyisocyanate (1), isocyanate-reactive compound (2) and compound (3) or polyol (2) and polyol (3) and water, preferably the amount of compound (2) or polyol (2) ranges from 2–20 parts by weight, the amount of compound (3) or polyol (3) ranges from 5–35 parts by weight and the amount of water ranges from 1 to 17 parts by weight, the remainder being polyisocyanate. This encompasses another aspect of the invention: if a cyclic polyisocyanate and more in particular an aromatic polyisocyanate and most in particular an MDI or polymethylene polyphenylene polyisocyanate is used the content of cyclic and more in particular of aromatic residues in the flexible foam is relatively high as compared to conventional flexible polyurethane foams. The foams according to the invention preferably have a content of benzene rings, derived from aromatic polyisocyanates, which is 30 to 56 and most preferably 35 to 50% by weight based on the weight of the foam. since polyols, polymer polyols, fire retardants, chain extenders and/or fillers which contain benzene rings may be used, the overall benzene ring content of the flexible foam may be higher and preferably ranges from 30 to 70 and most preferably from 35 to 65% weight as measured by calibrated Fourier Transform Infra Red Analysis.

In addition to the polyisocyanate, the isocyanate-reactive compounds and the blowing agent, one or more auxiliaries or additives known per se for the production of polyurethane foams may be used. Such optional auxiliaries or additives include foam-stabilizing agents or surfactants, for example siloxane-oxyalkylene copolymers and polyoxyethylene polyoxypropylene block copolymers, urethane/urea catalysts, for example tin compounds such as stannous octoate or dibutyltin dilaurate and/or tertiary amines such as dimethylcyclohexylamine or triethylene diamine and/or phosphates like $NaH_2PO_4$ and $Na_2HPO_4$, and fire retardants, for example halogenated alkyl phosphates such as tris chloropropyl phosphate, melamine and guanidine carbonate, anti-oxidants, UV stabilisers, anti-microbial and anti-fungal compounds and fillers like latex, TPU, silicates, barium and calcium sulphates, chalk, glass fibers or beads and polyurethane waste material.

In operating the process for making rigid foams according to the invention, the known one-shot, prepolymer or semi-prepolymer techniques may be used together with conventional mixing methods and the rigid foam may be produced in the form of slabstock, mouldings including foam in fabric and pour-in-place applications, sprayed foam, frothed foam or laminates with other materials such as hardboard, plasterboard, plastics, paper or metal or with other foam layers.

It is convenient in many applications to provide the components for polyurethane production in pre-blended formulations based on each of the primary polyisocyanate and isocyanate-reactive components. In particular, an isocyanate-reactive composition may be used which contains the auxiliaries, additives and the blowing agent in addition to the isocyanate-reactive compounds (2) and (3) in the form of a solution, an emulsion or dispersion.

The rigid foam is prepared by allowing the aforementioned ingredients to react and foam until the foam does not rise any more. Subsequently the foam may be crushed. It is however preferred to allow the rigid foam obtained to cool down to below 80° C., preferably below 50° C. and most preferably to ambient temperature prior to crushing. After rise curing of the foam may be continued as long as desirable. In general a curing period of 1 minute to 24 hours and preferably of 5 minutes to 12 hours will be sufficient. If desired curing may be conducted at elevated temperature. The rigid foam (i.e. before crushing) preferably has a density of 3–27 and most preferably of 3–18 kg/m³.

The rigid foam (i.e. before crushing) prepared has a substantial amount of open cells. Preferably the cells of the rigid foam are predominantly open.

The crushing may be conducted in any known manner and by any known means. The crushing may for instance be conducted by applying mechanical force onto the foam by means of a flat or pre-shaped surface or by applying variations of external pressure.

In most cases a mechanical force sufficient to decrease the dimension of the foam in the direction of the crushing by 1–90%, preferably by 50–90% will be appropriate. If desired crushing may be repeated and/or carried out in different directions of the foam. Due to the crushing the ball rebound increases considerably in the direction of the crushing. Due to the crushing the density of the foam may increase. In general this increase will not exceed 30% of the density before crushing.

Although it is difficult to give more precise directions for the crushing since it will inter alia depend on the density of the foam, the rigidity of the foam, the type of crushing device used, we believe those skilled in the art are sufficiently aware of the phenomenon of crushing of polyurethane foams that they will be able to determine the appropriate crushing manner and means with the above guidance, certainly in the light of the following examples.

After the crushing a novel flexible foam is obtained which has exceptional properties. Despite the fact that the foam is flexible, it does not show a significant change of the Young's storage modulus E' over a temperature range from −100° C. to +25° C., as described before. The foam shows even in the absence of flame retardant additives good fire retardant properties. The oxygen index of the foam prepared from aromatic polyisocyanates preferably is above 20 (ASTM 2863); Further it shows a Young's storage modulus at 25° C. of at most 500 kPa, preferably at most 350 kPa, most preferably between 10–200 kPa and a sag factor (CLD 65/25, ISO 3386/1) of at least 2.0, preferably at least 3.5 and most preferably of 4.5–10. CLD hysteresis loss values for the foams are below 55% and preferably below 50% (which is calculated by the formula $$\frac{(A-B)}{A} \times 100\%,$$

wherein A and B stand for the area under the stress/strain curve of the loading (A) and unloading (B) as measured according to ISO 3386/1). Still further these foams can be manufactured with a very low or even negative Poisson's ratio as determined by lateral extension studies under compression of the foams. Finally compression set values of the foams are generally low, preferably below 40% (ISO 1856 Method A, normal procedure).

If the $Tg^h$ is not too high the foam might be used in thermoforming processes to prepare shaped articles. Preferably the $Tg^h$ of the foam is between 80 and 180° C., most preferably between 80° C. and 160° C. for such thermoforming applications.

Further the foams show good load-bearing properties like compression hardness values without the use of external fillers together with a good resilience, tear strength and durability (fatigue resistance) even at very low densities. In conventional flexible foams often high amounts of filler need to be used to obtain satisfactory load-bearing properties. Such high amounts of fillers hamper the processing due to a viscosity increase.

The foams of the present invention may be used as cushioning material in furniture and automotive seating and in mattresses, as carpet backing, as hydrophilic foam in diapers, as packaging foam, as foams for sound insulation in automotive applications and for vibration isolation in general.

The invention is illustrated by the following examples.

EXAMPLE 1

A polyisocyanate mixture was prepared by mixing 56.6 parts by weight of polymeric MDI having an NCO value of 30.7% by weight and an isocyanate functionality of 2.7 and 43.4 parts by weight of a uretonimine modified MDI having an NCO value of 31% by weight, an isocyanate functionality of 2.09, a uretonimine content of 17% by eight and 2,4'-MDI content of 20% by weight.

An isocyanate-reactive composition was prepared by mixing 32.2 arts by weight (pbw) of polyethylene glycol having a molecular weight of 200, 4.5 pbw of ethylene glycol, 42.6 pbw of an EO/PO polyol having a nominal functionality of 2, an EO content of 20.2% by weight (all tipped) and hydroxyl value of 30 mg KOH/g, 5.5 pbw of diethanolamine, 14.5 pbw of water and 0.7 pbw of di-butyl-tin-dilaurate. This composition was an emulsion.

106.1 pbw of the polyisocyanate mixture and 46.9 pbw of the isocyanate-reactive composition (isocyanate index 75.5) were mixed for 13 seconds using a Heidolph™ mechanical mixer at a speed of 5000 rounds per minute (rpm). After mixing the reaction mixture was poured in an open 5 liter bucket and allowed to react. Prior to the pouring of the reaction mixture into the bucket, the inner walls of the bucket were greased with release agent Desmotrol™ D-10RT. 2½ minutes after the foam has stopped rising (foam rise time 70 seconds) the foam was taken out of the bucket and allowed to cool to ambient temperature. A rigid polyurethane foam was obtained. Core foam samples were then cut out of the centre of the foam for property evaluation. The free rise core density was 11 kg/m³ (ISO/DIS845). Then the samples were crushed by one compression (70% CLD) in the rise direction of the foam using an Instron™ mechanical tester mounted with flat plates.

After crushing a flexible foam was obtained having no major glass-rubber transition between −100° C. and +25° C. and having the following properties :

| | |
|---|---|
| free rise core density (ISO/DIS 845, kg/m³) | 13 |
| ball rebound (ISO8307, %), measured in the direction of crushing | 59 |
| tensile strength at break (ISO-1798, kpa) | 71 |
| elongation at break (ISO-1798, %) | 30 |
| tear strength (ISO/DIS 8067, N/m) | 70 |
| compression set (ISO 1856, method A, %) | 38 |
| CLD −25% (ISO 3386/1, kpa) | 3.2 |
| CLD = compression load deflection) | |
| CLD −40% (ISO 3386/1, kpa) | 5.2 |
| CLD −65% (ISO 3386/1, kpa) | 18.3 |
| CLD sag factor (ISO 3386/1) | 5.7 |
| CLD hysteresis loss (ISO 3386/1, %) | 48 |
| tan $\delta_{max}$ (−100° C. to +25° C.) (ISO/DIS 6721-5) | 0.06 |
| oxygen index (ASTM 2863, %) | 20.5 |
| Young's storage modulus ratio $\frac{E' - 100° C.}{E' + 25° C.}$ (ISO/DIS 6721-5) | 2.0 |
| Young's storage modulus at 25° C. (ISO/DIS 6721-5, kpa) | 180 |
| Benzene content, % by weight (calculated) | 43.5 |

Compression foam properties were measured in the rise/crushing direction of the foam.

DMTA-test

Measurements were carried out according to ISO/DIS 6721-5 on a Rheometric Scientific DMTA apparatus using a 3-point bending mode. Sample test dimensions were: length 1.0 cm, width 1.3 cm, thickness 0.4 cm. Applied strain amplitude 64×10⁻⁴ cm, frequency 1 Hz, heating rate 3° C./min. The foam samples were pre-conditioned at 23° C./50% RH for 24 hours prior testing. The foam samples were quenched to −120° C. (cooling rate 8.5° C./min) and held at that temperature for 5 minutes before heating of the sample was started.

EXAMPLE 2

Three isocyanate reactive blends (blend A, B and C) were prepared. Blend A was prepared by mixing 200 pbw of the EO/PO polyol of example 1 and 6.5 pbw of 'DABCO' T9 (catalyst from AIR PRODUCTS, DABCO is a trade mark). Blend B was prepared by mixing 75.5 pbw of polyethylene glycol with a molecular weight of 200 and 5.56 pbw of 'IRGANOX' 5057 ( an anti-oxydant from Ciba-Geigy Ltd., IRGANOX is a trademark). Blend C was prepared by mixing 23.5 pbw of triethylene glycol, 40.0 pbw of water and 0.6 pbw of monobasic sodium phosphate.

166.1 pbw of blend A, 65.2 pbw of blend B, 51.6 pbw of blend C and 617.1 pbw of the isocyanate blend of example 1 (isocyanate index 100) were mixed for 13 seconds using an 'Ytron' (trademark) mechanical mixer at a speed of 3500 rpm. After mixing the reaction mixture was poured in an open 50×50×30 cm³ wooden mould. Prior to pouring the mixture in the wooden mould, the inner walls were covered with paper. One hour after the foam had stopped rising (foam rise time 70 seconds) the foam was taken out of the mould and allowed to cool to ambient temperature. The foam was cut and crushed as in example 1. The free rise core density before crushing was 13 kg/m³.

After crushing a flexible foam was obtained having no major glass-rubber transition between −100° C. and +25° C. and having the following properties (test procedures as in example 1):

| | |
|---|---|
| free rise core density (kg/m³) | 15 |
| ball rebound (%) | 62 |
| tensile strength at break (kPa) | 67 |
| elongation at break (%) | 49 |
| compression set (%) | 31 |
| CLD-40% | 7.1 |
| Young's storage modulus ratio (E' −100° C./E' +25° C.) | 2.8 |
| Young's storage modulus (kPa) | 158 |
| benzene content, % by weight calculated | 42.6 |

EXAMPLE 3

Two isocyanate reactive blends (blend A and B) were prepared. Blend A was prepared by mixing 30 pbw of the EO/PO polyol of example 1, 0.3 pbw of 'DABOO' T9 and 0.3 pbw of 1-methyl-1-oxo-phospholene (a carbodiimide catalyst from Hoechst). Blend B was prepared by mixing 11.3 pbw of polyethylene glycol with a molecular weight of 200, 1.95 pbw of diethanolamine, 1.58 pbw of ethylene glycol and 4.5 pbw of water.

26.9 pbw of blend A, 17.3 pbw of blend B and 108.6 pbw of the isocyanate blend of example 1 (isocyanate index 123) were mixed for 13 seconds with a 'Heidolph' mechanical mixer at a speed of 5000 rpm. After mixing the reaction mixture was poured in an open 5 liter bucket and allowed to react. One hour after the foam has stopped rising (foam rise time 70 seconds) the foam was taken out of the bucket and allowed to cool to ambient temperature. A rigid polyurethane foam was obtained with a free rise density of 16 kg/m³. Attenuated total reflection Fourier transform infra red analysis showed the presence of carbodiimide groups (signal at 2140 cm⁻¹).

After crushing as described in example 1 a flexible foam having no major glass-rubber transition between −100° C. and +25° C. was obtained with the following mechanical properties (test procedures as in example 1):

| | |
|---|---|
| free rise core density (kg/m³) | 18 |
| ball rebound (%) | 48 |
| Young's storage modulus ratio (E' −100° C./E' +25° C.) | 2.5 |
| Young's storage modulus at 25° C. (kPa) | 126 |
| benzene content, % by weight calculated | 42.9 |

What is claimed is:
1. A process for preparing a rigid polyurethane foam by reacting:
   (1) a polyisocyanate;
   (2) an isocyanate reactive compound having an average equivalent weight of at most 374 and an average number of isocyanate-reactive hydrogen atoms of from 2 to 8;
   (3) an isocyanate-reactive compound having an average equivalent weight of more than 374 and an average number of isocyanate-reactive hydrogen atoms of from 2 to 6; and

(4) water, wherein a total weight of compound (1), compound (2), compound (3) and compound (4) represents 100 parts per weight, the amount of compound (2) ranges from 2–20 parts by weight relative to the total weight, the amount of compound (3) ranges from 5–35 parts by weight relative to the total weight and the amount of compound (4) ranges from 1–17 parts by weight relative to the total weight.

2. A Process for preparing a rigid polyurethane foam by reacting:

(1) a polyisocyanate;

(2) a polyol having a hydroxyl number of at least 150 mg KOH/g and average nominal hydroxyl functionality of from 2 to 8;

(3) a polyol having a hydroxyl number from 10 to less than 150 and average nominal hydroxyl functionality of from 2 to 8; and (4) water, wherein a total weight of compound (1), compound (2), compound (3) and compound (4) represents 100 parts per weight, the amount of compound (2) ranges from 2–20 parts by weight relative to the total weight, the amount of compound (3) ranges from 5–35 parts by weight relative to the total weight and the amount of compound (4) ranges from 1–17 parts by weight relative to the total weight.

3. The Process for preparing a rigid polyurethane foam as recited in claim 1, wherein the weight ratio of compound (2): compound (3) is 0.1 to 4:1.

4. The Process for preparing a rigid polyurethane foam as recited in claim 2, wherein the weight ratio of compound (2): compound (3) is 0.1 to 4:1.

* * * * *